United States Patent [19]

Lopez et al.

[11] Patent Number: 4,874,299
[45] Date of Patent: Oct. 17, 1989

[54] HIGH PRECISION PUMP

[75] Inventors: Benjamin L. Lopez, Golden; Steven A. Beard, Denver; Kirby Phillips, Lakewood, all of Colo.

[73] Assignee: Life Loc, Inc., Wheatridge, Colo.

[21] Appl. No.: 203,279

[22] Filed: Jun. 6, 1988

Related U.S. Application Data

[63] Continuation-in-part of Ser. No. 35,758, Apr. 8, 1987, Pat. No. 4,749,553.

[51] Int. Cl.$^4$ .............................................. F04B 43/14
[52] U.S. Cl. ...................................... 417/413; 310/24
[58] Field of Search ................... 417/413; 310/15, 17, 310/22, 23, 24

[56] References Cited

U.S. PATENT DOCUMENTS

| | | | |
|---|---|---|---|
| 12,364 | 1/1910 | Roberts et al. | 417/413 |
| 1,196,552 | 8/1916 | La Porte . | |
| 1,782,407 | 11/1930 | Carter . | |
| 1,926,074 | 9/1933 | Warnke . | |
| 2,027,879 | 1/1936 | Piscionere . | |
| 2,216,703 | 10/1940 | Ericson . | |
| 2,254,495 | 9/1941 | Randolph et al. . | |
| 2,898,860 | 8/1959 | Grober . | |
| 3,515,966 | 6/1970 | de Valroger . | |
| 3,588,291 | 6/1971 | Curwen et al. | 417/417 |
| 3,814,552 | 6/1974 | Guggenheim et al. . | |
| 4,370,107 | 1/1983 | Landis et al. . | |
| 4,518,317 | 5/1985 | Inoue | 417/45 |
| 4,562,385 | 12/1985 | Rabson | 318/135 |
| 4,607,627 | 8/1986 | Leber et al. . | |

FOREIGN PATENT DOCUMENTS 0043280 3/1986 Japan ................................. 417/417

Primary Examiner—Carlton R. Croyle
Assistant Examiner—D. Scheuermann
Attorney, Agent, or Firm—Gary M. Polumbus

[57] ABSTRACT

A precision pump for moving small volumes of fluid includes an electromagnet in which is reciprocally mounted an armature carrying a diaphragm on one end such that upon reciprocal movement of the armature an alternating high and low pressure can be created in a pumping chamber to move fluid through the pump. In one embodiment of the pump, the electromagnet drives the armature in one direction and a spring returns the armature to effect the reciprocating movement while in a second embodiment a pair of electromagnets are axially aligned and cooperate with a pair of magnets on the armature to alternately move the armature in a linear reciprocating motion as current is alternately applied to the electromagnets.

5 Claims, 4 Drawing Sheets

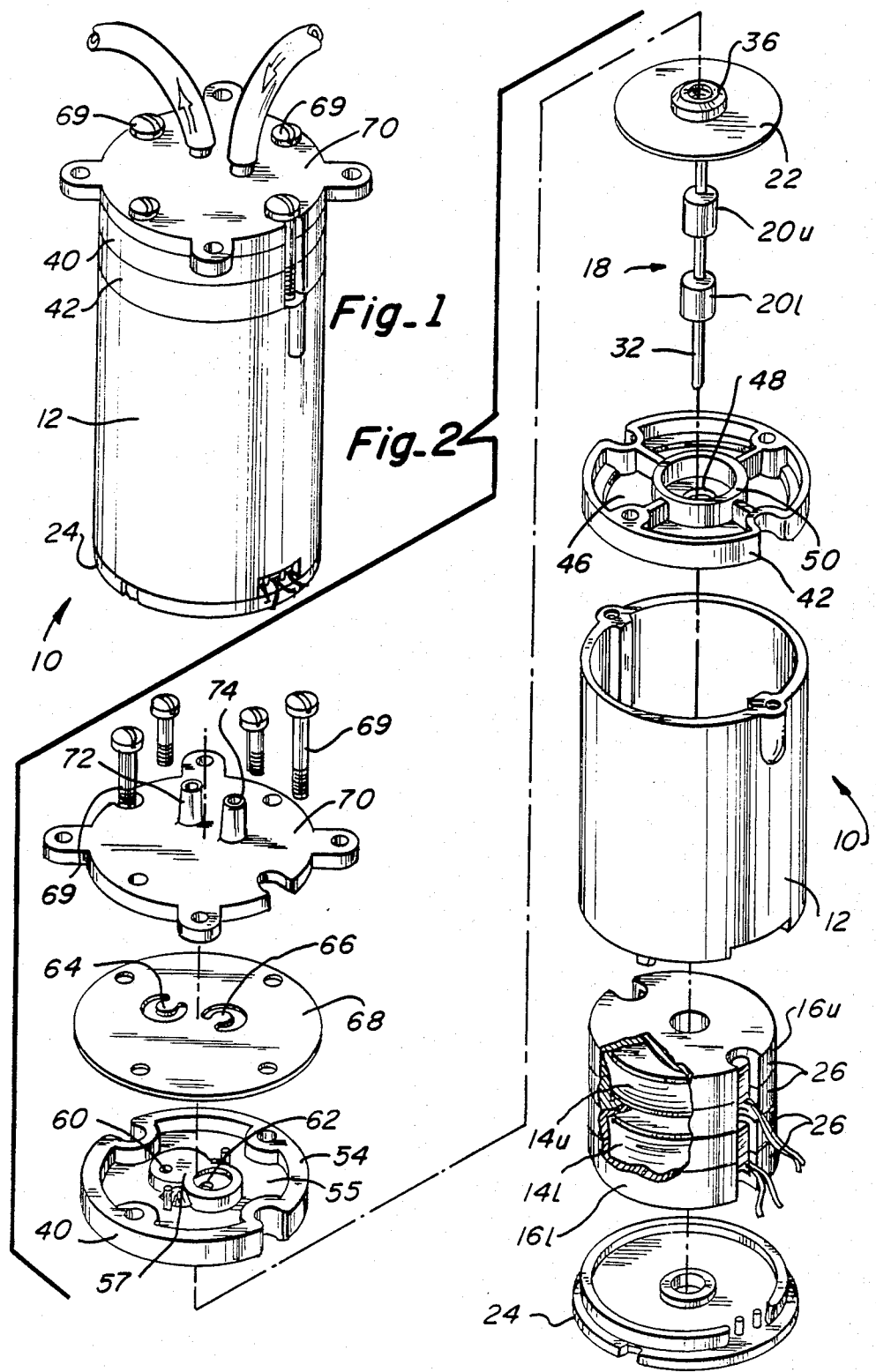

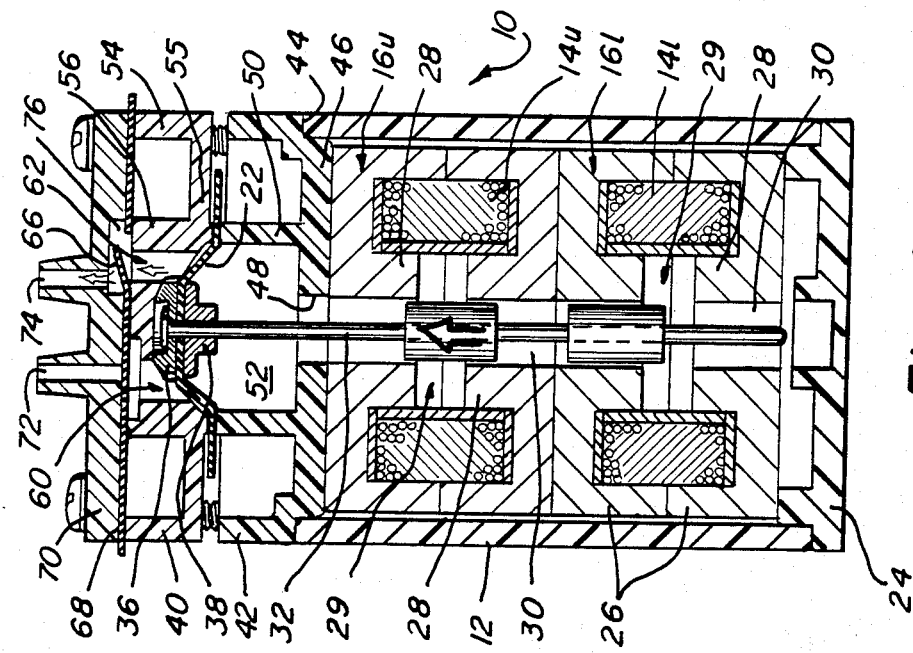
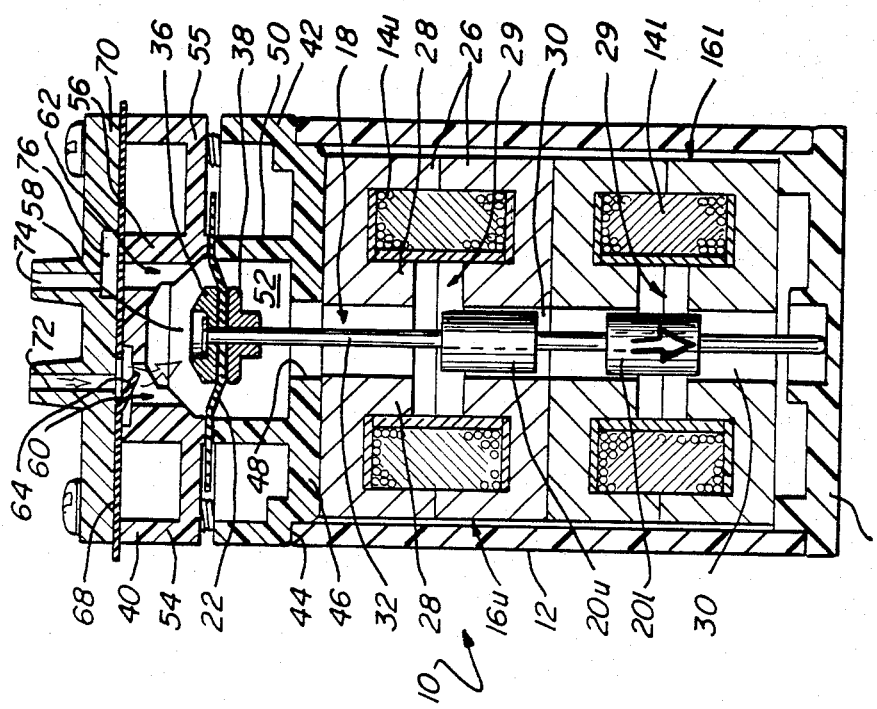

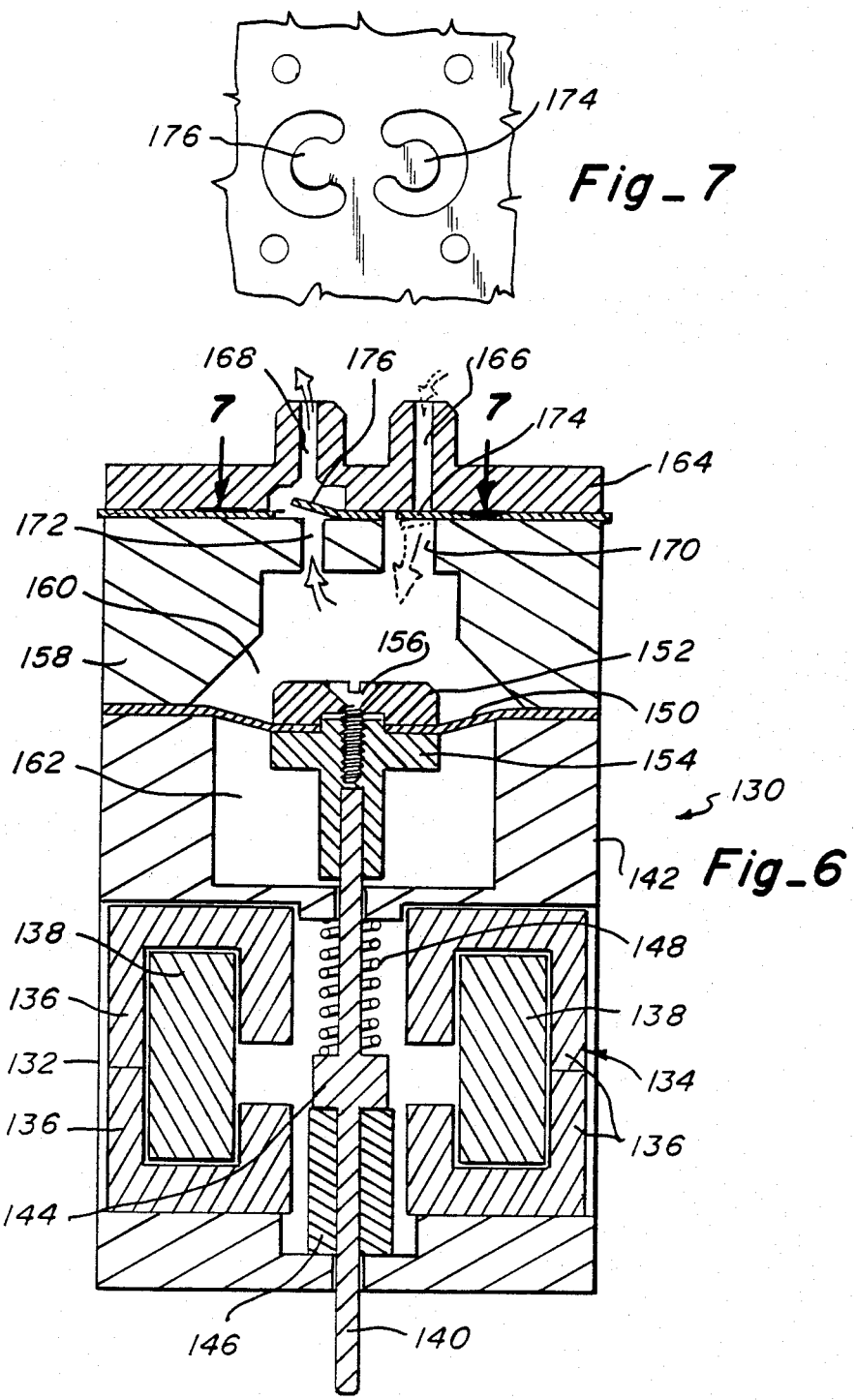

HIGH PRECISION PUMP

CROSS-REFERENCE TO RELATED APPLICATIONS

This application is a continuation in part of Ser. No. 035,758 filed Apr. 8, 1987 now U.S. Pat. No. 4,749,553, June 7, 1988, for Breath Alcohol Detector with Improved Compensation for Environmental Variables.

BACKGROUND OF THE INVENTION

1. Field of the Invention

The present invention relates generally to high precision pumps and more particularly to an electromagnetic pump adapted primarily for low volume usage.

2. Description of the Prior Art

Low volume pumps, at least those that sell for a reasonable price, are typically of the rotary type wherein a rotary motor drives a disk which in turn causes a rod having a diaphragm on one end thereof to reciprocate to create an alternating high pressure low pressure zone for moving fluid through the pump. The volume output of such pumps is solely dependent upon the voltage applied to the rotary motor and at low rpms the output of the pump is not as stable as is many times desired.

This drawback is partially due to the fact that the reciprocating rod has a single stroke which is not variable. Another drawback with rotary pumps is the fact that when a load is placed on the pump, it draws more current thereby draining the battery or other power source for the pump. Also, rotary pumps utilize numerous bearings which wear out creating maintenance demands which are frequently hard to meet and always frustrating to deal with.

It is an object of the present invention to provide a low volume pump which has a more precise output regardless of the flow level through the pump.

It is another object of the present invention to provide a low volume high precision pump that requires little or no maintenance and is efficient in operation.

SUMMARY OF THE INVENTION

The present invention relates to a high precision low volume electromagnetic pump that utilizes at least one magnetic coil to reciprocate an enclosed armature which has a diaphragm on one end that creates an alternating high pressure low pressure environment for moving fluid through the pump.

In a first embodiment of the present invention, a pair of aligned coils are utilized to reciprocally drive a single armature carrying two beads so that the armature is driven in one direction upon energization of one coil and driven in the opposite direction upon energization of the other coil. A diaphragm is disposed on one end of the armature for moving fluid through the pump.

In a second embodiment of the present invention, a single coil is utilized to drive an armature having a magnetic bead thereon in a reciprocating linear pattern. Energization of the coil drives the armature in one direction and resilient means return the armature upon deenergization of the coil. A diaphragm carried on one end of the armature is flexed also in a reciprocating manner to draw fluid into the pump and alternately expel fluid from the pump in a highly dependable manner.

Due to the extreme precision and controllability of the pump, among its many suitable uses are with mass spectometers, ionization and electrochemical sensors used in industrial hygiene and blood gas monitoring markets, and in the medical and scientific fields as a precision metering and drug injection pump.

Other aspects, features and details of the present invention can be more completely understood by reference to the following detailed description of a preferred embodiment, taken in conjunction with the drawings, and from the appended claims.

BRIEF DESCRIPTION OF THE DRAWING

FIG. 1 is a perspective view of one embodiment of the pump of the present invention.

FIG. 2 is an exploded perspective view of the pump illustrated in FIG. 1 with parts removed for clarity.

FIG. 3 is an enlarged vertical section of the pump showing the armature at or near the end of one stroke.

FIG. 4 is a vertical section similar to FIG. 3 with the armature at or near the end of an opposite stroke.

FIG. 6 is a verticle section through a second embodiment of the present invention.

FIG. 7 is section taken along line 7—7 of FIG. 6.

DETAILED DESCRIPTION OF THE PREFERRED EMBODIMENTS

Figure 5:
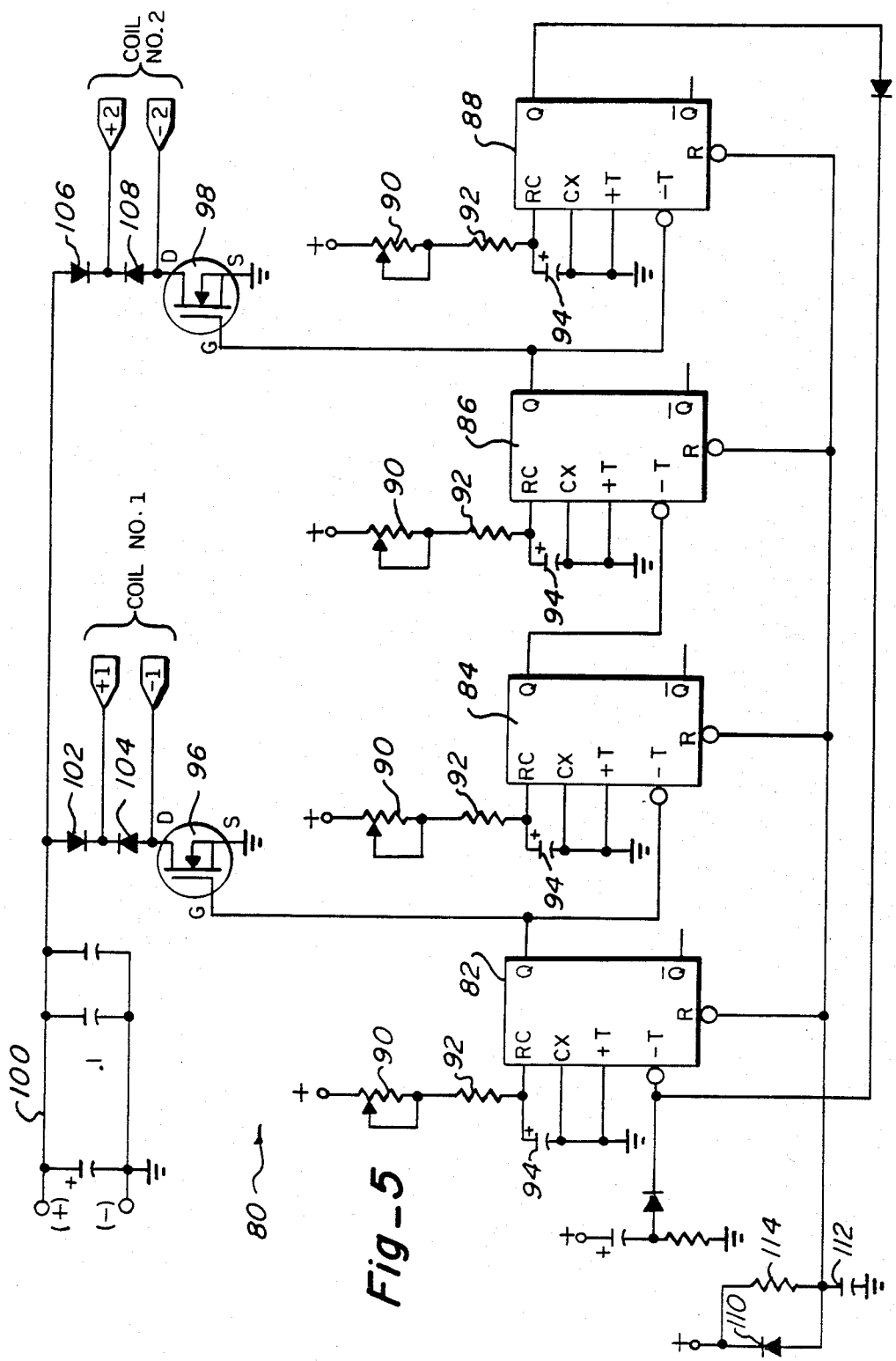
FIG. 5 is a diagramatic circuit diagram of the power means for the pump illustrated in FIGS. 1-4.

With reference first to FIGS. 1 and 2, a first embodiment 10 of the pump of the present invention is illustrated. The pump 10 includes an outer body or case 12 in which a pair of superimposed coils $14u$ and $14l$ mounted in ceramic cores $16u$ and $16l$ respectively are disposed for reciprocally driving an armature 18 having a pair of beads $20u$ and $20l$ thereon. The beads are adapted to react electromagnetically with respective ones of the coils to assist the armature in moving a flexible diaphragm 22 carried on the upper end of the armature to effect the passage of fluid through the pump.

The case 12 is preferably made of a plastic material such as NORELL and is of generally cylindrical configuration with open ends. A lower end cap 24 is provided for closing the lower end of the case and is secured thereto in any suitable manner. The lower end cap is adapted to support the magnetic cores and is also made of a plastic material such as NORELL.

The magnetic cores $16u$ and $16l$ as best seen in FIGS. 3 and 4 are preferably made of a ceramic material of high magnetic permeability with a characteristic of the material being a rapid build-up and decay of magnetic field. Each magnetic core is comprised of two component half segments 26 which are identical in configuration and when placed in abutting face to face relationship define a cavity in which an associated coil $14u$ or $14l$ is disposed and retained. Each half segment is generally cylindrical in configuration having a closed end and an open end and the open ends are placed in confronting relationship to define the enclosed core. Each half segment 26 includes a central hub 28 around which the coil is disposed but the hub has a height of slightly less than the half segment itself thereby defining a gap 29 between the hubs of confronting half segments. This gap is referred to as an air gap and has a direct bearing on the operation of the pump as will be apparent from the description that follows.

The hub 28 of each half segment has a central cylindrical axial passage 30 therethrough adapted to receive the armature 18, as will be described later, with the passage 30 of each core being in axial alignment so that the armature can extend through both cores.

The armature 18 is a very low mass rod 32 carrying a pair of longitudinally or axially spaced beads 20u and 20l of high magnetic permeability which are firmly attached to the rod for unitary movement therewith. The location of the beads on the rod are important to the effective operation of the pump as will be more apparent with the description that follows.

The armature 18 has a length sufficient to extend from the lower extent of the lower core 16l through the open upper end of the case 12. The upper end of the armature has the flexible circular diaphragm 22 affixed thereto. The flexible diaphragm 22 could be made of any suitable plastic or rubber material and is confined on the upper end of the armature by upper and lower connector members 36 and 38 respectively which pinch the diaphragm there between. The upper and lower connector members are fixed to the upper end of the armature in any suitable manner.

Disposed on the upper end of the case 12 is a compression block member 40 which overlies an intermediate case member 42 with the intermediate case member being positioned upon the upper end of the case and adapted to retain the two core members 16u and 16l in position within the case. The intermediate case member is of generally disk shaped configuration having an external peripheral groove 44 adapted to receive the upper end of the cylindrical wall of the case. The intermediate case member has a lower generally circular wall 46, the lower face of which abuts the top of the upper core 16u so as to confine the cores within the case between the intermediate case member and the lower end cap 24. The circular bottom wall 46 of the intermediate case member has a centrally disposed circular opening 48 therethrough which is in alignment with the passages through the hubs 28 of the cores thereby defining a path in which the armature 18 is free to reciprocate. A cylindrical rib 50 is also provided in the center of the intermediate case portion 42 which is upstanding relative to the bottom circular wall 46 and defines an interior chamber 52 within which the connector members 36 and 38 are free to move. The upper circular edge of the cylindrical rib 50 is adapted to support a portion of the diaphragm 22 which is pinched there against by the compression block member 40.

The compression block member 40 is also of generally disk shaped configuration having an outer peripheral cylindrical wall 54 in alignment with the cylindrical wall of the intermediate case member 42 and the cylindrical wall of the case 12. The compression block member has a bottom wall 55 in which is formed a generally frustoconically shaped recess 56 forcing a generally figure eight shaped protuberance 57 on the top surface of the bottom wall 55. The recess 56 defines a pump or pumping chamber 58 opening downwardly and being separated from the interior chamber 52 by the diaphragm 22. The pump chamber is closed on its upper most extent with the exception of an intake port 60 and an exhaust port 62 which are disposed on opposite sides of the chamber.

A pair of flapper valves 64 and 66 overlie the inlet and exhaust ports respectively of the pump chamber 58 and are part of a flexible valve sheet 68 which is disposed across the upper end of the compression block member 40 and held in place by a top cap 70 and a plurality of fasteners 69 which extend through the superimposed parts into the case 12. The top cap 70 is a solid circular disk having inlet and exhaust ports 72 and 74 respectively in alignment with the inlet and exhaust ports 60 and 62 of the compression block member. The flapper valves themselves are flexible tabs formed internally of the valve sheet 68 as illustrated in FIG. 6 and lie in alignment with the inlet and exhaust ports of the compression block member and the top cap.

The flapper valve 64 which is in alignment with the intake ports is permitted to flex downwardly into the pump chamber 58 to allow fluid to flow into the chamber but flexing movement in the opposite direction is prevented by abutment with the bottom of the top cap 70. The other flapper valve 66 which is in alignment with the exhaust ports of both the compression block member and the top cap is allowed to flex into a chamber 76 defined in the top cap to allow fluid to flow from the pump chamber into the chamber 76 and subsequently out the exhaust port 74 of the top cap but is prevented from flexing inwardly into the pump chamber 58 by abutment with the figure eight shaped protuberance 57 on the compression block member.

The armature 18 is retained in a predetermined orientation at its upper end by the diaphragm 22 and along its length by the two beads 20u and 20l which are sized to slide within the passages through the hubs 28. If desired, bearings (not shown) can be placed near the upper and lower ends of the armature to better guide the armature movement and to extend the life of the pump. It will therefore be appreciated that the armature is disposed for linear reciprocating movement within the cores 16u and 16l in a manner that will cause the diaphragm 22 to flex into and out of the pump chamber 58 thereby raising and lowering the pressure in the pump chamber to draw fluid through the inlet port 60 and expel the fluid through the outlet port 62 from the chamber in a known manner.

As will be appreciated, the coils 14u and 14l and the highly magnetically permeable cores, define electromagnetic means in the form of electromagnets which selectively attract the highly permeable magnetic metal beads 20u and 20l toward the air gap at the center of the associated core when the associated coil is energized. As will be further appreciated by reference to FIG. 3, the metal beads are spaced on the rod 32 of the armature a distance such that when the lower bead 20l is substantially disposed near the center air gap of the lower core 16l the upper bead 20u is disposed slightly below the center air gap of the upper core 16u. At or near the opposite extreme of a stroke of the armature as seen in FIG. 4, the upper bead 20u is substantially centrally disposed within the upper core 16u while the lower bead 20l is disposed immediately above the center of the lower core 16l.

In this orientation, with the armature 18 being initially disposed in the lower position of FIG. 3, upon energization of the upper coil 14u, the upper bead is drawn upwardly toward the center air gap of the upper core after the lower coil has been deenergized. In an opposite manner, when the upper coil is deenergized and the lower coil energized, the lower bead is drawn into the center air gap of the lower core thereby pulling the armature into the lower position of FIG. 3.

This operation results from the fact that the cores 16u and 16l concentrate the magnetic fields generated by the coils 14u and 14l into the gap 29 in the center of the coils. The magnetic field produced from the current flowing through the coil attracts the associated bead on the armature toward a centered position in the gap defined at the center of the core. By attaching the beads to the armature at preselected locations and controlling the current pulses through the coils, a reciprocal motor is produced. Due to the fact that the diaphragm 22 is connected to the armature, the reciprocal movement of the motor so defined causes fluid to move through the pump through the alternate creation of high pressure and low pressure in the pump chamber 58. The effect of the diaphragm in moving fluid through the pump is well known in the art and an explanation thereof is set forth later in the description of the second embodiment of the present invention.

One example of means for selectively energizing coils 14u and 14l of the pump is illustrated in the circuit 80 of FIG. 5. The circuit 80 also incorporates means for selectively controlling the on, or energization time period, of each of the coils individually, as well as selectively controlling the length of the relaxation, or off time, of each of the coils. The circuit 80 incorporates four conventional one-shot multivibrators 82, 84, 86 and 88. A resistive-capacitive timing circuit consisting of a variable resistor 90, a fixed resistor 92 and a capacitor 94 is connected to the RC, CX and plus T terminals of each one-shot. This RC circuit 90, 92 and 94 controls the on time of each of the one-shots. The length of the on-time is established by adjustment of the resistent value of the variable resistor 90, and by the size of the capacitor 94. Because a separate RC timing circuit is connected to each of the one-shots, the on time of each of the one-shots can be separately established.

During the on time of each of the one-shots, the Q output terminal is forced high and remains high during the duration of the on time period. At the end of the on time period, established by the RC timing circuit, the Q output terminal goes low. The high to low transition triggers the next one-shot in series as a result of the signal of the Q output terminal of the preceding one-shot being applied to the negative T input terminal of the following one-shot. A closed loop arrangement is established because the signal from the Q output terminal of one-shot 88 is applied to the negative T input terminal of the one-shot 82.

The signal at the Q output terminal of one-shot 82 is applied to the gate terminal of a FET transistor 96. The FET 96 has its drain terminals connected to the conductor 98 which forms the first coil of the pump. Similarly, the Q output terminal of one-shot 86 is connected to the gate terminal of a second FET 98. The drain terminal of the FET 98 is connected to the second coil of the pump. When the one-shot 82 is turned on, the signal at the Q output terminal renders the FET 96 conductive. Current time from a conductor 100 is conducted through a diode 102, the electrical conductor forming the first coil through the FET 96, to reference potential. At the end of the on time period of one-shot 82, the signal at the Q output terminal goes low, thereby turning off FET 96 and triggering the one-shot 84. The current flowing through the first coil is aborted by the action of the diode 104. At the termination of the on time of the one-shot 84, the negative going signal from its Q output terminal triggers one-shot 86. The high signal from the Q output terminal triggers FET 98, thereby causing current to flow through the diode 106 and the second coil. At the termination of the on time period of one-shot 86, the FET 98 turns off and the diode 108 absorbs the current flowing in the second coil. The one-shot 88 is turned on, and remains on until the expiration of its on time period, at which time the negative going signal from the Q terminal triggers the one-shot 82. In this manner, the progress just described continually repeats.

Circuitry including a diode 110, a capacitor 112 and a resistor 114 is connected to the reset terminals of each of the one-shots, for the purpose of establishing an initial uniform state in all of the one-shots when the circuit is first powered on. The initially predetermined state allows the circuit 80 to function in the manner described.

The RC timing circuit associated with each of the one-shots allows the on time of each of the one-shots to be separately established and controlled. In this manner, the on and off time of each of the coils 14u and 14l is separately established. One-shot 82 establishes the on time for the first coil, while one-shot 84 establishes the off time of the first coil. One-shot 86 establishes the on time for the second coil while one-shot 88 establishes the off time of the second coil. By separately controlling the on and off times of each of the coils, it is possible to regulate the volume, pressure or current utilization of the pump.

Another advantage of the circuit 80 is that the amount of driving force or driving effect created by the energization of the upper and lower coils of the pump can be controlled within certain voltage ranges of the power supplied on conductor 100. With a greater voltage applied on conductor 100, more current will flow through each of the coils when the FET's 96 and 98 are turned on. The higher current causes a stronger electromagnetic force which more readily drives the armature of the pump in opposite directions. Depending upon the on and off times, the extent of current flowing through each of the coils will determine whether the bead attached to the armature shaft actually centers in the core gap of an associated core, or whether the resistence of the fluid being pumped or the inertia of the armature prevent the bead from centering in the gap prior to the time that the off time period for each coil occurs.

Thus, the circuit 80 shown in FIG. 5 provides two separate but interrelated methods of controlling the volume of fluid moving through the pump. These separate interrelated control techniques are very useful for precisely establishing a volumetric flow through the pump even when relatively small quantities of volumetric flow are desired. Of course, these two separate but interrelated techniques are separately establishing the on and off times for each of the coils, and controlling the amount of driving current conducted through each of the coils by controlling the voltage on the power supply conductor 100.

An alternative to utilizing the four one-shots connected sequentially in a closed loop as shown in FIG. 5, is to directly drive the FET's 96 and 98 by outputs from a microprocessor driver under the control of software within the microprocessor. The software within the microprocessor can establish the on and off times by utilizing the clock rate of the microprocessor, and supplying the appropriate signals for driving the FET's accordingly.

In a second embodiment of the pump of the present invention shown in FIG. 6, the pump 130 is again seen to be an electromagnetically reciprocated diaphragm type pump. The pump 130 includes an exterior plastic case 132, which is preferably made of NORELL. Within the case 132 is positioned a magnetic core 134 comprised of half segments 136. Within the center of the core 134 is an electrical coil 138. A non-magnetic shaft 140 is positioned along the axis of the annular structure defined by the core 134 and the coil 138. The shaft 140 is retained for axial movement by an opening in the case 132 at one end, and by another opening in an intermediate case portion 142 at the other end. The intermediate case portion 142 is also preferably made of plastic such as NORELL. In the mid-section of the shaft 140 is a shoulder 144. A ferromagnetic or other magnetic material bead 146 is located between the shoulder 144 and the case 132. A spring 148 is positioned between the shoulder 144 and the opening in the case 132. The spring 148 normally biases the shaft downwardly, as shown in FIG. 7. The length of the bead 146 establishes the maximum extent of downward movement (as shown in FIG. 7) of the shaft 140.

When the coil 138 conducts current, the bead 146 is attracted toward the core gap at the center of the core 134. The attraction creates a force which is applied on the shoulder 144 to move the shaft 140 upwardly, as viewed in FIG. 7. When the current flow in the coil 138 is terminated, the spring 148 applies force on the shoulder 144 to force the shaft downwardly, as viewed in FIG. 7. Thus, when the coil 138 is energized, the shaft 140 is moved in one direction, and when the coil is deenergized, the spring 148 reciprocates by moving the shaft in the opposite direction. In this manner, the shaft 140 is reciprocated in the pump 130.

A flexible diaphragm 150 is connected to one end of the shaft 140. A connector member 152 is connected to the end of the shaft 140, and a thrust washer 154 is connected to the connector member 152 by a screw 156. The diaphragm 150 is positioned between the connector member 152 and the thrust washer 154. The reciprocal movement of the shaft 140 deflects the diaphragm member 150. As is illustrated in FIG. 6, the diaphragm 150 is deflected as a result of the downward position of the shaft 140. When the coil 138 is energized, the shaft 140 moves in an upward direction as shown in FIG. 6.

The exterior edges of the diaphragm 150 are held in position by a compression block 158 pressed by screws (not shown) against the intermediate case portion 142. The interior of the compression block 158 and the diaphragm 150 define a pump chamber 160 through which fluid can be moved as the diaphragm 150 is reciprocated. The interior of the intermediate case portion 142 defines an interior chamber 162 within which the connector 152 moves. The chamber 162 is vented to the exterior of the pump as a result of clearance between the shaft 140 and the openings through which it moves in the case portions 132 and 142.

A top cap 164 is connected to the compression block 158, preferably by the same screws (not shown) which connect the compression block to the case 142. The top cap 164 includes an inlet passage 166 and an outlet passage 168 which are aligned with an inlet port 170 and an outlet port 172 in the compression block.

In order to obtain a pumping action, it is necessary to limit the fluid flow to a single direction through the pump chamber 160. One way valves, such as flapper valves 174 and 176, are respectively positioned in the inlet 170 and outlet 172 of the pump chamber 160. The flapper valves 174 and 176 work in the conventional manner to create one-way fluid flow through the pump chamber 160. Upon movement of the shaft 140 downwardly to deflect the diaphragm 150 to expand the volume within the pump chamber 160, the inlet flapper valve 194 is opened by the slight negative pressure within the pump chamber 160 to allow fluid to be drawn into the chamber through the top cap 164 and inlet passage 166. The slight negative pressure within the pump chamber 160 holds the exhaust flapper valve 176 in a closed position, thereby assuring that fluid is drawn through the inlet 170 into the pump chamber 160 but not exhausted. When the shaft 140 moves in the other direction a slight positive pressure is created in the pump chamber 160. The slight positive pressure closes the inlet flapper valve 174 and opens the exhaust flapper valve 176, thereby allowing the gas within the pump chamber 160 to be pushed out through the outlet 172 to the outlet passage 168. When the flapper valves 174 and 176 are closed, they seat and set against surfaces on the top cap 164 and the compression block 158 to create a substantial fluid tight seal, in a conventional manner. When the flappper valves are open, they are deflected off of the seating surfaces to allow space for fluid to flow through the valves.

A power supply for the pump 130 could be supplied by many suitable circuits but by way of example, one-half of the circuit shown in FIG. 5 could be utilized. In such an instance, only two one-shots would be utilized rather than the four one-shots described for powering the first embodiment of the present invention.

From the description set forth above, it will be appreciated that the extent and rate of reciprocation can be precisely controlled in either embodiment of the invention and is directly related to the volumetric fluid flow conducted by the pump. Very precise volumetric flow rates are thereby established, and these volumetric flow rates are important to many utilizations of a high precision low volume pump.

One of the desirable features of the pump of the present invention is its programably determinable flow rate, according to the frequency of electrical energization of the coil or coils. Another advantage is its relative lack of moving parts, and thus its relative reliability. Its life expectancy is very high, compared to other types of pumps which require constant maintenance and replacement. The pump can also be produced at a relatively low cost.

Although the present invention has been described with a certain degree of particularity, it is understood that the present disclosure has been made by way of example, and changes in detail or structure may be made without departing from the spirit of the invention, as defined in the appended claims.

I claim:

1. An improved pump comprising in combination:
  a reciprocally acting motor means comprising a shaft retained for reciprocal movement, first and second magnet means attached to the shaft at predetermined axially spaced locations, first and second electromagnetic means arranged in axial alignment with said shaft and associated with the first and second magnet means respectively, to alternately attract the first and second magnet means when energized,
  a flexible diaphragm operatively connected with the shaft to be deflected upon movement of the shaft, and means defining in cooperation with the diaphragm a pumping chamber in which the volume of the chamber varies in relation to the deflection of the diaphragm,
  an inlet to the pump chamber, an inlet one-way valve which allows the fluid to flow into the pumping chamber and prevents fluid flow through the inlet out of the pumping chamber, an outlet from the pumping chamber, and an outlet one-way valve which allows the fluid to exit the pumping chamber and prevents fluid flow through the outlet into the pumping chamber, and means for alternately energizing and deenergizing the first and second electromagnetic means at a predetermined rate to reciprocate the shaft in alternatively opposite directions with each energization of one electromagnetic means and to deflect the diaphragm at a related predetermined rate to obtain a predetermined volumetric flow through the pumping chamber, and said first and second electromagnetic means each include a core gap into which the associated magnet means is drawn when the electromagnetic means is energized, and the core gaps of the first and second electromagnetic means are spaced axially a greater predetermined distance than the axial predetermined spacing of the first and second magnet means on the shaft.

2. The improved pump of claim 1 wherein each said electromagnetic means includes a magnetic core and a coil formed by an electrical conductor positioned to induce a magnetic flux in the core, and wherein the core is characterized by a rapid build-up and a rapid decay of magnetic flux.

3. The improved pump of claim 2 wherein said coil is disposed within said magnetic core.

4. The improved pump of claim 3 wherein each said electromagnetic means comprises an annularly shaped core positioned relative to the shaft and having an opening therein within which the associated magnet means moves, the core gap being located axially within the opening.

5. The improved pump of claim 4 wherein the inlet and the outlet one-way valves are each flapper valves.

* * * * *